US010350405B2

(12) United States Patent
Suwito et al.

(10) Patent No.: US 10,350,405 B2
(45) Date of Patent: Jul. 16, 2019

(54) SYSTEM, METHOD AND TOOL FOR IMPLANTING PERIPHERAL NERVE ELECTRODE CUFF

(71) Applicant: BIOTRONIK SE & Co. KG, Berlin (DE)

(72) Inventors: Wantjinarjo Suwito, West Linn, OR (US); Isaac Kreft, Sherwood, OR (US); Andrew B. Kibler, Lake Oswego, OR (US); Jeffrey A. von Arx, Lake Oswego, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 218 days.

(21) Appl. No.: 15/434,213

(22) Filed: Feb. 16, 2017

(65) Prior Publication Data

US 2017/0266436 A1   Sep. 21, 2017

Related U.S. Application Data

(60) Provisional application No. 62/309,480, filed on Mar. 17, 2016.

(51) Int. Cl.
*A61N 1/05* (2006.01)
*A61B 5/00* (2006.01)
*A61N 1/36* (2006.01)

(52) U.S. Cl.
CPC .......... *A61N 1/0556* (2013.01); *A61B 5/6877* (2013.01); *A61N 1/36053* (2013.01)

(58) Field of Classification Search
CPC ................ A61N 1/0556; A61N 1/0551; A61N 1/36053; A61B 5/6877
See application file for complete search history.

(56) References Cited

U.S. PATENT DOCUMENTS

| 2003/0040785 | A1 | 2/2003 | Maschino et al. |
| 2006/0030919 | A1 | 2/2006 | Mrva et al. |
| 2011/0184437 | A1* | 7/2011 | Udo ...................... A61N 1/0556 606/129 |
| 2013/0231726 | A1 | 9/2013 | Johnson et al. |
| 2014/0188202 | A1 | 7/2014 | Zarembo et al. |

OTHER PUBLICATIONS

European Search Report and Annex to the European Search Report on European Patent Application No. EP 17 15 6244.0, dated Jun. 2, 2017 (6 pages).

* cited by examiner

*Primary Examiner* — Paula J Stice
(74) *Attorney, Agent, or Firm* — Buchanan Ingersoll & Rooney PC

(57) ABSTRACT

System, method, and tool for implanting an electrode cuff. The system can include a cuff and a slider implement, where the cuff is temporarily retained within and/or onto the slider implement by a retainer mechanism during implantation. The cuff can be structured to exhibit a natural rolled shape, but can be resiliently bendable so as to flex from the rolled shape while having a tendency to move back to the rolled shape. The cuff can be releasably secured to a portion of the slider implement, which may include holding the cuff in an unrolled shape. The cuff can then be positioned adjacent the nerve. The retainer mechanism can then be actuated to allow the cuff to advance towards its naturally rolled shape, thereby wrapping around the nerve.

19 Claims, 9 Drawing Sheets

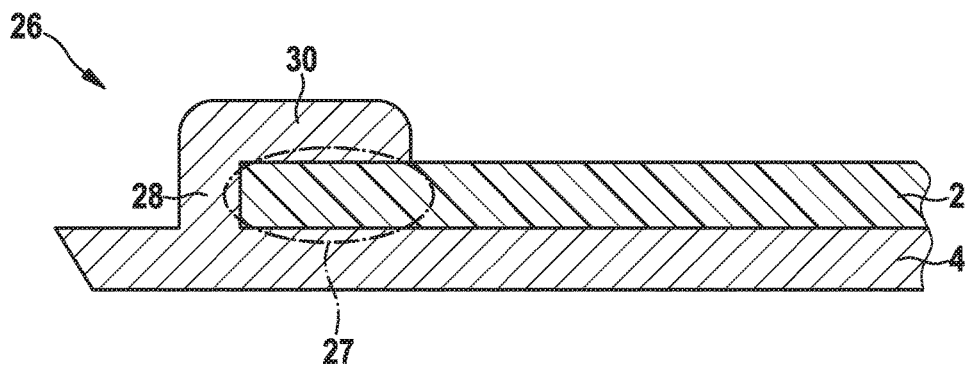
FIG. 2
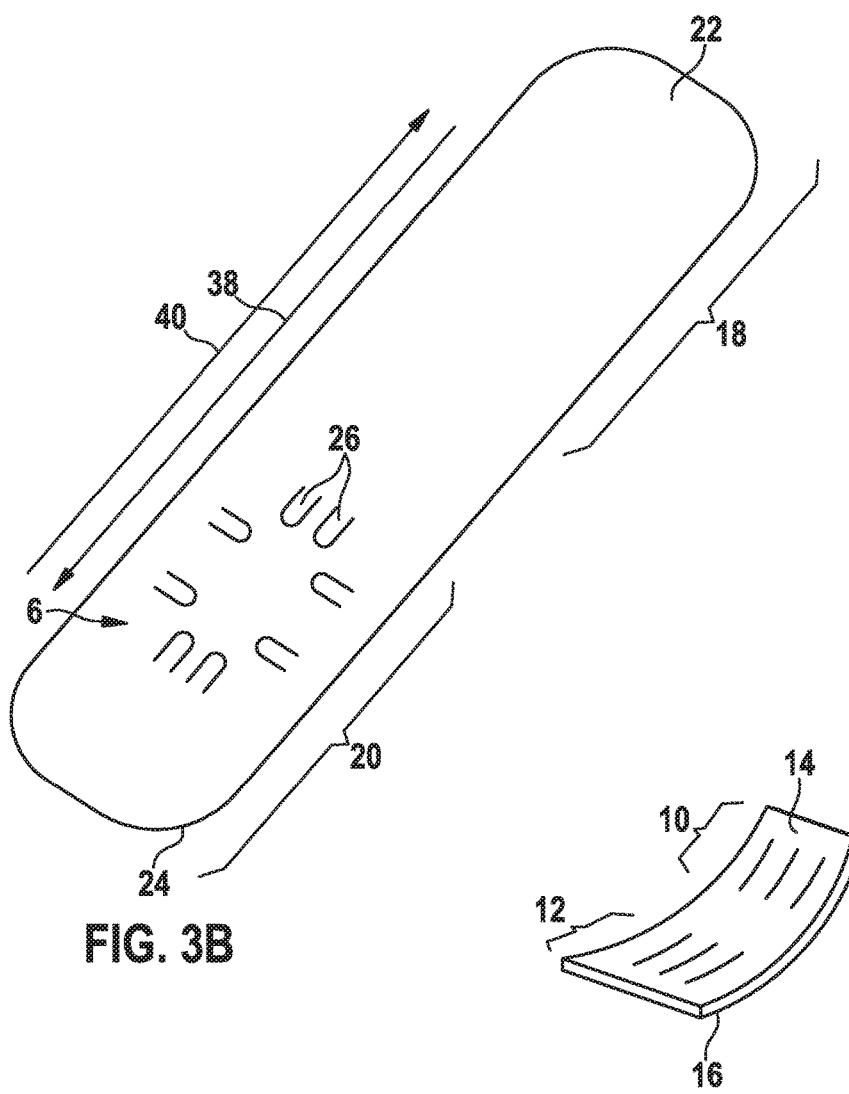
FIG. 3B
FIG. 3A

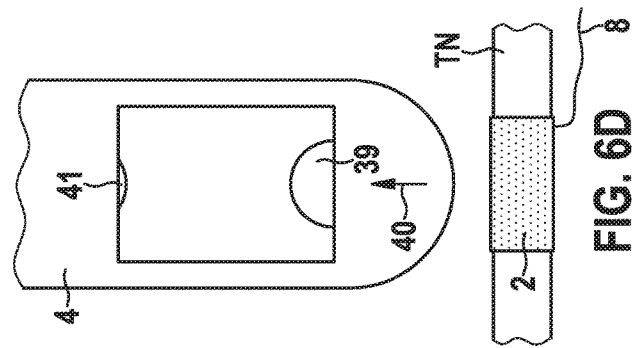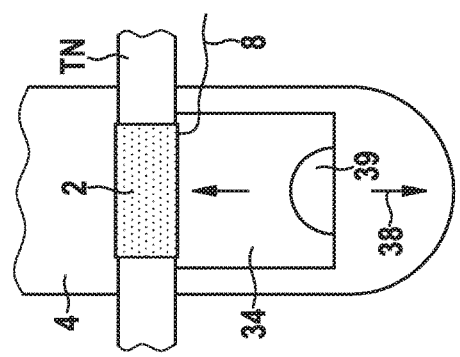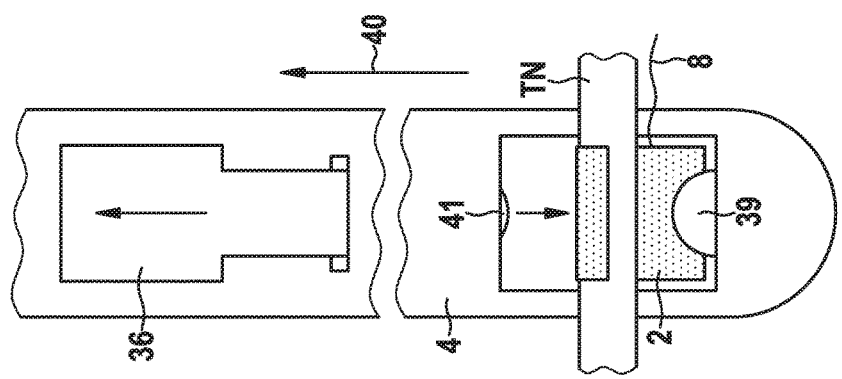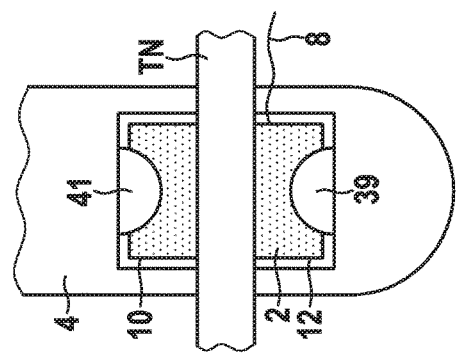

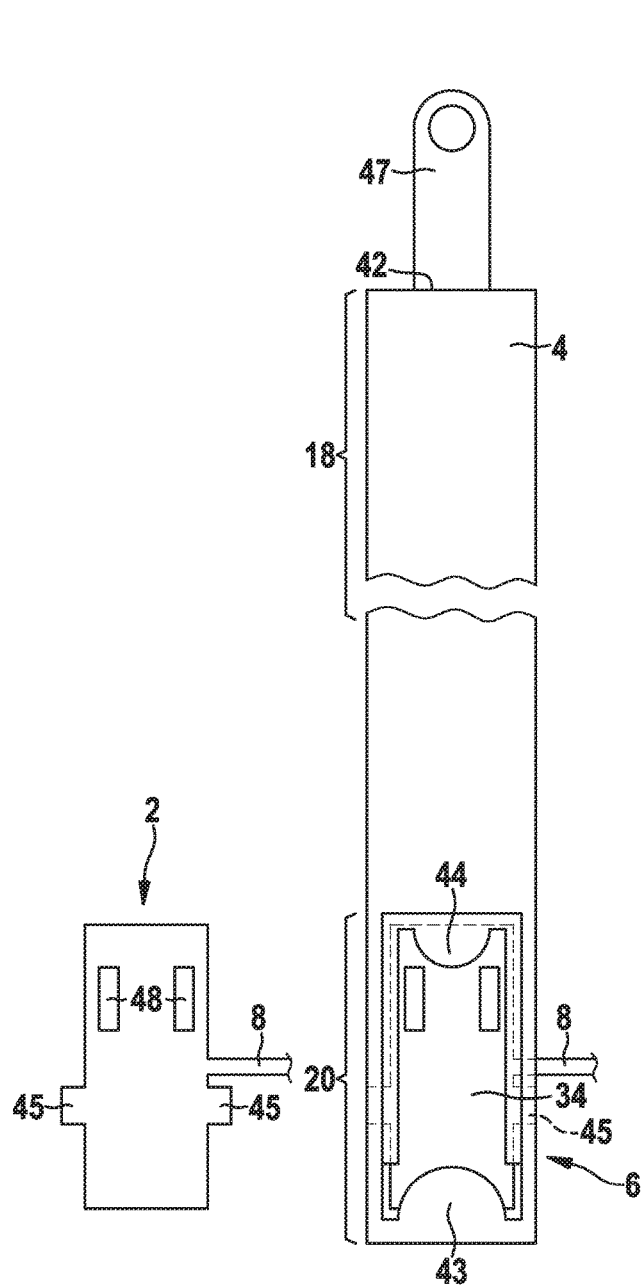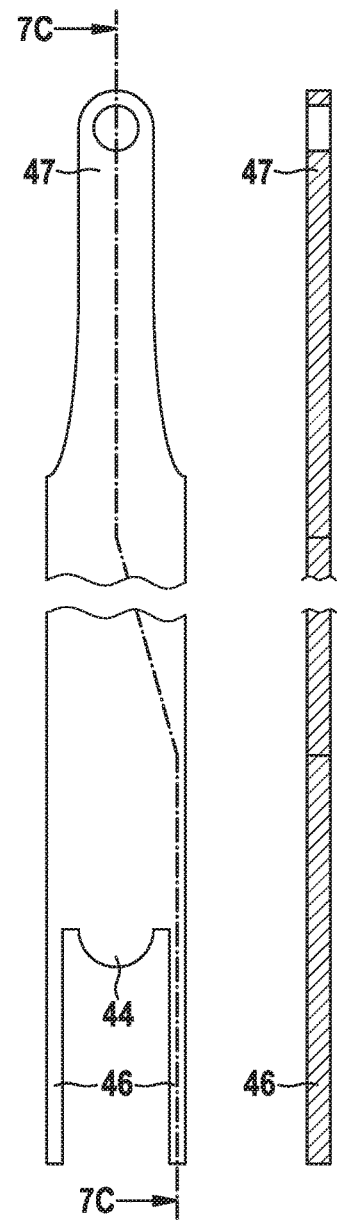
FIG. 7A   FIG. 7B   FIG. 7C

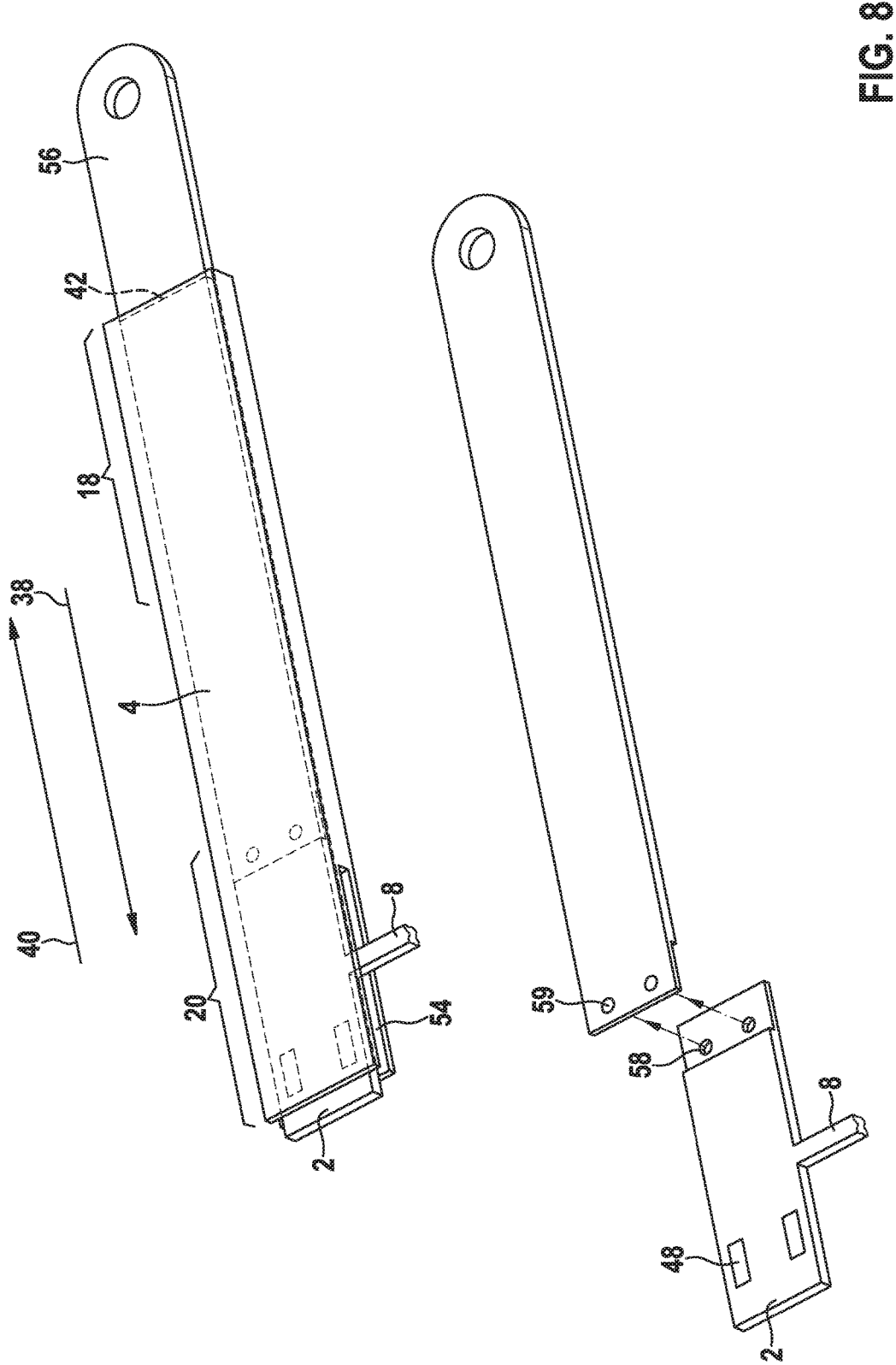

SYSTEM, METHOD AND TOOL FOR IMPLANTING PERIPHERAL NERVE ELECTRODE CUFF

CROSS-REFERENCE TO RELATED APPLICATIONS

This patent application claims the benefit of co-pending U.S. Provisional Patent Application No. 62/309,480, filed on Mar. 17, 2016, which is hereby incorporated by reference in its entirety.

FIELD OF THE INVENTION

Embodiments of the disclosed invention relate to a system and a method for implanting and delivering an electrode cuff. The disclosed invention can include a flat, flexible implement fed behind a peripheral nerve for delivery of the electrode cuff, where the electrode cuff may be used for nerve stimulation and/or recording neurograms.

BACKGROUND OF THE INVENTION

Implantation of a nerve cuff for peripheral nerve stimulation, and specifically vagus nerve stimulation ("VNS"), can be a cumbersome process. It typically involves careful excising of the vagus or vagal nerve from its sheath and manually coiling an electrode-bearing device (e.g., electrode cuff) around the nerve. The desire to minimize scar size can lead surgeons to create a small incision, which leaves little room to manipulate multiple surgical implements while handling and deploying the electrode cuff.

Known system and methods generally consist of a coil-shaped nerve electrode cuff that is manually wrapped around the vagus nerve using standard surgical forceps and other implements. The proximity of this operation to the carotid artery, jugular vein, and other vessels may provide additional hazards. For example, employing such techniques can result in an increased risk of puncturing one of these vessels or severing the vagus nerve itself. Generally, such procedures require slow and deliberate actions on the part of the surgeon. Thus, the manual nature of wrapping the cuff can be time consuming and may increase the risks of nerve and vasculature damage.

The present invention is directed toward overcoming one or more of the above-identified problems.

SUMMARY OF THE INVENTION

The system can include a cuff and a slider implement, where the cuff is temporarily retained within and/or onto the slider implement by a retainer mechanism during implantation. The cuff can be structured to exhibit a natural rolled shape, but can be resiliently bendable so as to flex from the rolled shape while having a tendency to move back to the rolled shape. The cuff can be releasably secured to a portion of the slider implement, which may include retaining the cuff in an unrolled shape. The cuff and at least a portion of the slider implement may then be inserted through an incision and into an incision site (e.g., cuff implant site) to position the cuff adjacent the target nerve (e.g., a vagus nerve). The retainer mechanism can then be actuated to allow the cuff to advance towards its naturally rolled shape, thereby wrapping around the nerve. The slider implement can then be removed from the incision, and the incision closed, to complete the surgical procedure.

In one implementation, the system can be used to deploy a cuff around a nerve by following the exemplary steps. After shaving and sterile preparation of the skin over the patient's cuff implant site on the neck, and the implantable pulse generator ("IPG") implant site on the chest, an incision can be made at the cuff implant site (i.e., neck incision or incision site) and muscular tissue may be dissected and retracted to reveal the vagus nerve in the carotid arterial sheath. Optionally, at this time the IPG pocket may be prepared as well. The carotid sheath can be carefully incised along, for example, a 3 centimeter length, and the vagus nerve may be freed within this incision. The cuff may then be loaded in the slider implement (i.e., delivery tool, cuff deployment tool, deployment tool, or tool), if not preloaded, and the delivery tool may be slid under the vagus nerve. Once positioned as desired, the delivery tool can be actuated to release a portion of the cuff that contains stimulating electrodes and is designed to wrap immediately around the vagus nerve. Once contact is confirmed, the delivery tool can be actuated further to fully release the cuff onto the vagus nerve, and the delivery tool may be slid from under the cuff and the vagus nerve. Tunneling may be performed at this time from the neck incision to the IPG incision, and the lead body may be drawn through, such that the cuff at the distal end of the lead is not disturbed, and the lead body connector lies near in the IPC incision site. The lead impedance may be tested as necessary. Lead anchors can be placed on a lead strain relief loop in the neck as necessary, which may be sutured to connective tissue for fixation. Next, the IPG can be unpackaged and connected to the lead connector, where testing can be performed, and the IPG may be placed with further strain relief loop of lead body in the patient's IPG pocket. Both incision sites are sutured closed in layers, which may be the final step.

The present invention can be used for implanting a peripheral nerve cuff with a simplified surgical procedure using a method that minimizes risk of nerve stress and damage. Further, the system and method can minimize manipulation of the cuff, which can prevent damage of the electrodes of the cuff. This can be achieved by facilitating implantation of a full electrode cuff without cumbersome and risky manual deployment processes. In some implementations, it is preferred for the cuff to be released in a staged fashion, which can prevent sudden complete deployment.

Overall, the inventive system and method can provide for a slider implement with a flat shape (i.e., low cross section), delivery of the cuff in an unrolled shape (i.e., maintain a low profile during insertion), and precise control of electrode position at deployment. Thus, the present invention can allow for a more repeatable, safe, and simple implantation process. In addition, the cuff and deployment tool can be presented in a pre-assembled, ready-to-deploy state. Further benefits can include a cuff geometry that is no longer limited to a spiral shape. Thus, designers can have more flexibility regarding the number and position of electrodes placed within and/or onto the cuff. Moreover, the delivery tool can unroll or roll cuff smoothly without damage to electrodes, contacts, or interconnects.

In an exemplary embodiment, a system for implanting a nerve cuff can include a nerve cuff comprising a flat, flexible material having distal and proximal ends, wherein the nerve cuff is biased to a naturally coiled shape; and a slider implement configured to deploy the nerve cuff and wrap the nerve cuff around a target nerve, the slider implement comprising: an elongated member having a slider proximal end and a slider distal end; a retainer mechanism provided on the slider distal end, the retainer mechanism configured to temporarily retain the nerve cuff in an uncoiled state within and/or on the slider implement, wherein the slider distal end is configured to insert into an incision and position the nerve cuff adjacent the target nerve, and wherein actuation of the retainer mechanism releases the nerve cuff from the slider implement such that the nerve cuff transitions from the uncoiled state to the coiled state allowing the nerve cuff to wrap around the target nerve. The nerve cuff may include an electrode nerve cuff comprising at least one electrode, which can be brought in electrical contact with the target nerve or target nerve tissue. The retainer mechanism can include at least one tab formed on a surface of the slider distal end; and actuation of the retainer mechanism comprises manipulation of the at least one tab. Further, the retainer mechanism can include a debossed section formed in the slider implement at the slider distal end configured for receiving the nerve cuff in the uncoiled state, a fixed tab disposed on the slider distal end and extending over the debossed section; and a movable tab provided on a distal end of a pull tab received in a slot formed in the slider implement, the movable tab extending into the debossed section to maintain the nerve cuff in the debossed section, and wherein the pull tab is movable to retract the movable tab into the slider slot to release the nerve cuff for deployment about the target nerve. In other embodiments, the retainer mechanism can include a debossed section formed in the slider implement at the slider distal end configured for receiving the nerve cuff in the uncoiled state, a fixed tab disposed on the slider distal end and extending over the debossed section; a movable tab provided on a distal end of a pull tab received in a slot formed in the slider implement, the movable tab extending into the debossed section to maintain the nerve cuff in the debossed section; and arms extending from the pull tab distal end past the movable tab, the arms extending into the debossed section to maintain the nerve cuff in the debossed section, wherein the pull tab is movable to retract the movable tab into the slider slot to release an end the nerve cuff for deployment about the target nerve, wherein the arms engage the nerve cuff permitting the nerve cuff to coil only up to a midpoint, wherein further movement of the pull tab causes teeth formed on the arms to engage tabs on the nerve cuff to disengage the nerve cuff from the fixed tab enabling the nerve cuff to fully wrap around the target nerve. The arms may be located at the opposite side edges of the pull tab distal end (opposite arms) with the movable tab located in between. In further embodiments, the retainer mechanism can include a cuff-retention slot formed into the slider distal end, the cuff retention slot comprising an aperture used to slidably receive and temporarily retain the electrode cuff in the unrolled position within the slider implement; wherein a slider slot is formed into the slider implement extending from the slider proximal end to the slider distal end and leading into the cuff-retention slot; wherein the system further comprises a plunger slidably received in the slider slot; and movement of the plunger in a forward proximal-distal direction causes the nerve cuff retained within the cuff retention slot to exit the cuff-retention slot by exiting the slider distal end, and as the electrode cuff exits the slider distal end it begins to transition to the coiled position. The nerve cuff and plunger may include cooperating mating elements which are configured to enable the plunger to pull the nerve cuff into the cuff retention slot and push the nerve cuff out of the cuff retention slot for deployment about the target nerve. In some embodiments, the system can include at least one assist-string attached to the nerve cuff, wherein the at least one assist-string enables controlled coiling of the nerve cuff when deployed about the target nerve.

In an exemplary embodiment, a tool for implanting a nerve cuff can include a slider implement configured to deploy the nerve cuff and wrap the nerve cuff around a target nerve, the slider implement comprising: an elongated member having a slider proximal end and a slider distal end; a retainer mechanism provided on the slider distal end, the retainer mechanism configured to temporarily retain the nerve cuff in an uncoiled state within and/or on the slider implement, wherein the slider distal end is configured to insert into an incision and position the nerve cuff adjacent the target nerve, and wherein actuation of the retainer mechanism releases the nerve cuff from the slider implement such that the nerve cuff transitions from the uncoiled state to the coiled state allowing the nerve cuff to wrap around the target nerve. In some embodiments the nerve cuff can include an electrode nerve cuff comprising at least one electrode, which can be brought in electrical contact with the target nerve or target nerve tissue. The retainer mechanism may include at least one tab formed on a surface of the slider distal end; and actuation of the retainer mechanism comprises manipulation of the at least one tab. In some embodiments, the retainer mechanism can include a debossed section formed in the slider implement at the slider distal end configured for receiving the nerve cuff in the uncoiled state, wherein a fixed tab disposed on the slider distal end and extending over the debossed section; and a movable tab provided on a distal end of a pull tab received in a slot formed in the slider implement, the movable tab extending into the debossed section to maintain the nerve cuff in the debossed section, and wherein the pull tab is movable to retract the movable tab into the slider slot to release the nerve cuff for deployment about the target nerve. Further, the retainer mechanism can include a debossed section formed in the slider implement at the slider distal end configured for receiving the nerve cuff in the uncoiled state, a fixed tab disposed on the slider distal end and extending over the debossed section; a movable tab provided on a distal end of a pull tab received in a slot formed in the slider implement, the movable tab extending into the debossed section to maintain the nerve cuff in the debossed section; and arms extending from the pull tab distal end past the movable tab, the arms extending into the debossed section to maintain the nerve cuff in the debossed section, wherein the pull tab is movable to retract the movable tab into the slider slot to release an end the nerve cuff for deployment about the target nerve, wherein the opposing arms engage the nerve cuff permitting the nerve cuff to coil only up to a midpoint, wherein further movement of the pull tab causes teeth formed on the arms to engage tabs on the nerve cuff to disengage the nerve cuff from the fixed tab enabling the never cuff to fully wrap around the target nerve. The arms may be located at the opposite side edges of the pull tab distal end (opposite arms) with the movable tab located in between. In some embodiments, the retainer mechanism can include a cuff-retention slot formed into the slider distal end, the cuff retention slot comprising an aperture used to slidably receive and temporarily retain the electrode cuff in the unrolled position within the slider implement; wherein a slider slot is formed into the slider implement extending from the slider proximal end to the slider distal end and leading into the cuff-retention slot; wherein the tool further comprises a plunger slidably received in the slider slot; wherein movement of the plunger in a forward proximal-distal direction causes the nerve cuff retained within the cuff retention slot to exit the cuff-retention slot by exiting the slider distal end, and as the electrode cuff exists the slider distal end it begins to transition to the coiled position. The nerve cuff and plunger may include cooperating mating elements which are configured to enable the plunger to pull the nerve cuff into the cuff retention slot and push the nerve cuff out of the cuff retention slot for deployment about the target nerve. The tool can further include at least one assist-string attached to the nerve cuff, wherein the at least one assist-string enables controlled coiling of the nerve cuff when deployed about the target nerve. The retainer mechanism may hold the nerve cuff into a shape conformal with the slider distal end.

In an exemplary embodiment, a method for implanting a nerve cuff can include temporarily securing a nerve electrode cuff in an uncoiled position within a debossed section formed in a slider implement at a slider distal end via a retainer mechanism, wherein the retainer mechanism comprises a fixed tab connected to the slider implement, and a movable tab provided on a distal end of a pull tab received in a slot formed in the slider implement, the fixed tab and movable tab extending into the debossed section and engaging the nerve cuff to temporarily maintain the nerve cuff in the debossed section. An incision can be created into a body of a being and excising a target nerve to create an incision site either before or after the electrode cuff is temporarily secured to the retainer mechanism. At least a portion of the slider implement and the nerve cuff can be inserted through the incision and advancing the nerve cuff into the incision site so that the nerve cuff is placed adjacent to the excised target nerve. The movable tab can be moved back into the slot to release a proximal end of the nerve cuff. The slider implement can be pushed further into the incision thus releasing the distal end of the nerve cuff from the fixed tab thereby permitting the nerve cuff to wrap around the target nerve. The slider implement can then be removed from the incision site. The nerve cuff may include an electrode nerve cuff comprising at least one electrode, which can be brought in electrical contact with the target nerve or target nerve tissue. Further, the method may include: causing the nerve cuff to unroll from its naturally rolled position; temporarily securing the nerve cuff in an unrolled position within and/or on a slider implement via a retainer mechanism; creating an incision into a body of a being and excising a target nerve to create an incision site either before or after the electrode cuff is secured to the retainer mechanism; inserting at least a portion of the slider implement and the electrode cuff through the incision and advancing the nerve cuff into the incision site so that the nerve cuff is placed adjacent to the excised target nerve; actuating the retainer mechanism, allowing the nerve cuff to advance toward its naturally rolled position, wherein transitioning from the unrolled position to the rolled position is uninterrupted or performed in a staged fashion; allowing the nerve cuff to wrap around the target nerve; and removing the slider implement from the incision site.

While these potential advantages are made possible by technical solutions offered herein, they are not required to be achieved. The presently disclosed invention can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following Figures, in which:

FIG. 2 is a partial view of a tab of an embodiment of a retainer mechanism that may be used with a slider implement according to the present invention.

FIG. 3A is an embodiment of an exemplary cuff in an intermediate position between a rolled position and an unrolled position, and FIG. 3B is a slider implement that may be used with the inventive system.

FIGS. 6A-6D show exemplary implementation steps that may be used to deploy a cuff with the inventive system.

FIGS. 7A-7C show an embodiment of the inventive system with a retention slide as part of the retainer mechanism, wherein FIG. 7A shows the inventive system comprising a slider element and, a retention slider and a cuff, wherein FIG. 7B shows the retention slider in detail, and wherein FIG. 7C shows the retention slider in a sectional view along dotted line in FIG. 7B.

FIG. 8 shows an embodiment of the inventive system a plunger as part of the retainer mechanism.

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Figure 1:
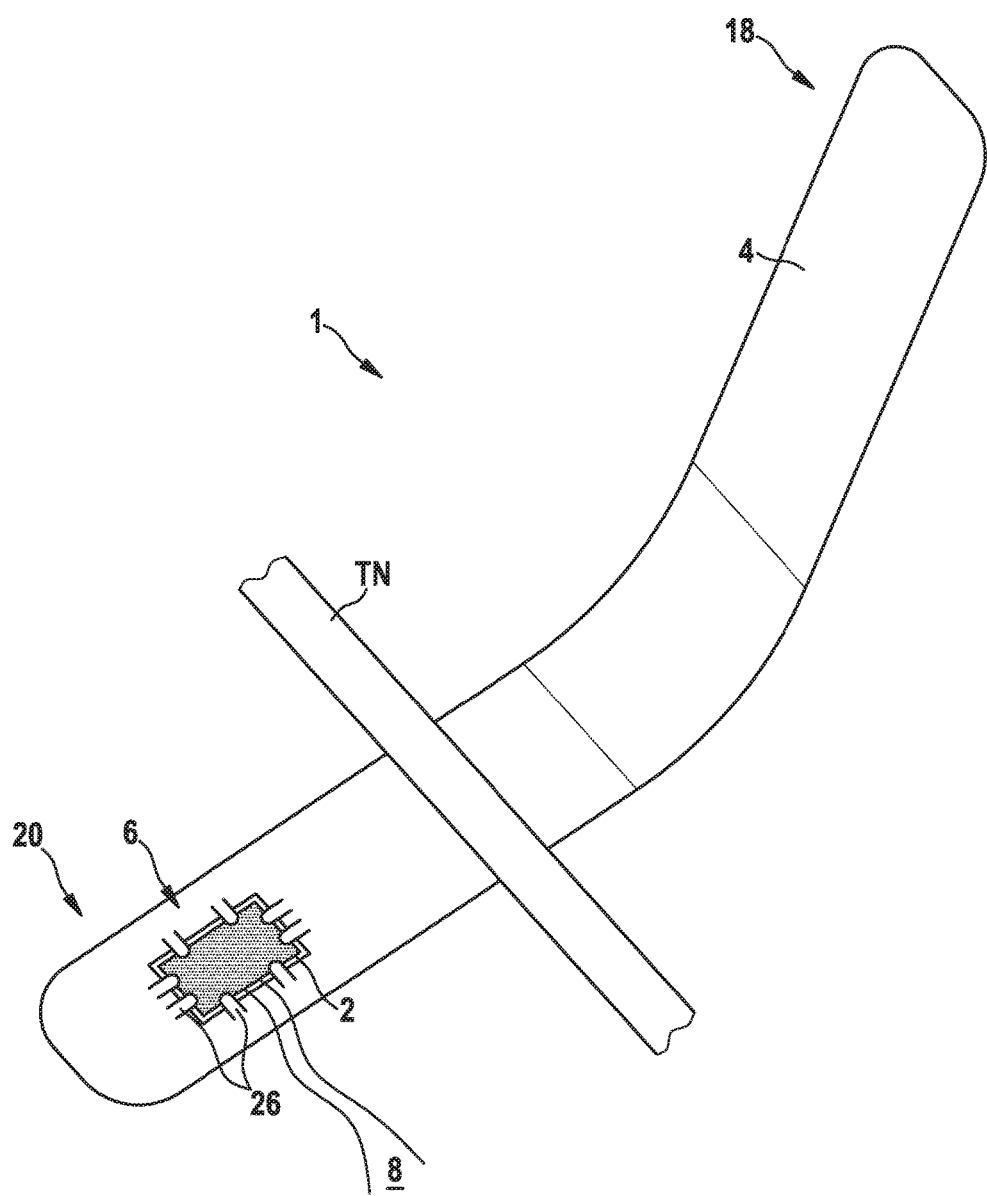
FIG. 1 is an exemplary embodiment of the inventive system showing a cuff being deployed behind a nerve by a slider implement.

Referring to FIGS. 1-3, the system 1 can include a cuff 2 and a slider implement 4, where the cuff 2 is temporarily retained in and/or on the slider implement 4 in an unrolled state by a retainer mechanism 6 during implantation. Once held in place by the slider implement 4, the cuff 2 and at least a portion of the slider implement 4 may be inserted through an incision and into an incision site to position the cuff 2 adjacent a target nerve TN (e.g., a vagus nerve). The retainer mechanism 6 can then be actuated to allow the cuff 2, which is manufactured in a naturally rolled shape, to wrap around the target nerve TN. The slider implement 4 can then be removed from the incision to complete the surgical procedure.

In some embodiments, cuff 2 can include an electrode-bearing device, which may be an electrode cuff 2 (cuff electrodes 48 shown in FIG. 7A). The cuff 2 can be fabricated from a flat, flexible, resilient material that is formed or biased into a coiled or arcuate shape so as to exhibit a naturally rolled shape (e.g. cuff can be made of silicone). For example, the cuff 2 can exhibit a rolled or coiled shape, but can be caused to unroll, uncoil and/or flatten with the application of force without plastically deforming so as to resiliently curl back to a rolled shape in the absence of such force. The cuff 2 can also be fabricated from a flexible thin-film substrate (e.g., liquid crystal polymer (LCP) or Polyimide) with metal (e.g., stainless steel or MP35N) electrode leads 8 embedded therein or attached thereto. The cuff 2 can further include electrical circuitry and/or electrical interconnects leading to electrical circuitry, where the electrical circuitry may facilitate nerve stimulation and/or neurogram recording. Thus, the cuff 2 can be a nerve cuff electrode that is in a rolled up preshape or preform. For implantation, this preform can be temporarily removed.

As shown more clearly in FIG. 3A, the cuff 2 can include a cuff proximal end 10, a cuff distal end 12, a cuff upper surface 14, and a cuff bottom surface 16. The cuff proximal end 10 is defined herein as being an end that is most proximal to a surgeon during implantation of the cuff 2. The cuff distal end 12 is defined herein as being an end that is most distal to the surgeon during implantation of the cuff 2. The cuff upper surface 14 can be a surface that is intended to face toward and make contact with the target nerve TN about which the cuff 2 is to be wrapped around (i.e., the vagal nerve). Thus, the cuff 2 upper surface is the concave portion of the cuff 2 and/or the surface that the cuff bottom surface 16 is rolled upon to generate the rolled position. The cuff bottom surface 16 is the convex portion of the cuff 2 and/or the surface that is facing radially outward when the cuff 2 is in the rolled position.

The slider implement 4 can be a tool used to securely, but temporarily, hold the cuff 2 in an unrolled position. In some embodiments, the slider implement 4 includes a flexible member that is structured to be inserted in or through an incision and position the cuff 2 adjacent the target nerve TN. This may include being structured to feed a portion of the slider implement 4 securing the cuff 2 under the target nerve TN. It is envisioned for the slider implement 4 to be thin and narrow to better accommodate the compromising space of the incision site. Further, the thin and narrow configuration can also prevent inadvertent contact with, and thus injury to, surrounding vessels, nerves, and tissue.

As shown in FIG. 3B, in some embodiments, the slider implement 4 can be an elongated member having a slider proximal end 18, a slider distal end 20, a slider upper surface 22, and a slider bottom surface 24. The slider proximal end 18 is defined herein as being an end that is most proximal to a surgeon during implantation of the cuff 2, which may include the end that is grasped by a surgeon's hands. The slider distal end 20 is defined herein as being an end that is most distal to the surgeon during implantation of the cuff 2, which may include the end that spearheads the insertion of the slider implement 4 through the incision. The slider implement 4 may be a rigid member, a semi-rigid member, or a combination of rigid and semi-rigid components. The slider implement 4 can be constructed from plastic, polymer material, metal, composite material, etc. For example, the slider implement 4 can be constructed from a biocompatible plastic material such as Polytetrafluoroethylene or Polyethylene. The slider implement 4 (or a section of it) can be coated with a soft material (e.g. silicone) to help minimize the risk of damaging the target nerve TN during use. A portion of the slider implement 4 can include the retainer mechanism 6, which can be structured to releasably secure the cuff 2 within and/or onto a portion of the slider implement 4. The retainer mechanism 6 is located at or near the slider distal end 20.

In general, the cuff 2 can be temporarily secured in and/or to the slider implement 4 by the retainer mechanism 6. This may cause the cuff 2 to unroll and become flat and/or conform to a shape of the slider implement 4. For example, securing the cuff 2 to the retainer mechanism 6 may cause the cuff 2 to conform to a shape of the slider distal end 20. Alternatively, the cuff 2 can be caused to unroll manually and then secured within and/or onto the slider implement 4 by the retainer mechanism 6. Thus, the retainer mechanism 6 can be used to temporarily secure the cuff 2 into and/or onto the slider implement 4 and/or temporarily hold the cuff 2 in an unrolled position. Additionally or alternatively, the cuff 2 can be pre-loaded onto the retainer mechanism 6 at a factory, and shipped to the field in this pre-loaded and releasable or temporarily secured configuration. Either before or after the cuff 2 is secured to the retainer mechanism 6, an incision can be made into a body of a being and the target nerve TN can be excised to create an incision site. At least a portion of the slider implement 4 and the cuff 2 can be inserted through the incision, where the slider distal end 20 may be used to spearhead the insertion. The slider distal end 20 and the cuff 2 can then be further advanced into the incision site so that the cuff 2 may be placed adjacent to the excised target nerve TN. This may include positioning the cuff 2 under the target nerve TN (e.g., vagal nerve—see FIG. 1). Placing the cuff 2 underneath the target nerve TN may be done to prevent an obstruction to the view of the surgeon while performing the implantation. The retainer mechanism 6 can then be actuated to allow the cuff 2 to advance toward its naturally rolled position and roll around the target nerve TN. The proximity with which the cuff 2 is placed to the target nerve TN can allow the cuff 2 to wrap around the target nerve TN, which may include enveloping or encapsulating a portion of the target nerve TN. Thus, the release of the cuff 2 in such a manner can facilitate delivery of the cuff 2 by allowing it to return to its naturally rolled shape around the target nerve TN. The release of the cuff 2 can be performed in a staged fashion. This may be achieved with the use of assist-strings 32 (see FIGS. 4A-4B) to ease the transition from the unrolled position to the rolled position. Alternatively, the release of the cuff 2 from the unrolled position to the rolled position can be uninterrupted. The slider implement 4 can then be removed from the incision site.

When held in the unrolled position by the retainer mechanism 6, the cuff 2 can conform to a shape of the slider distal end 20. This not only opens the cuff 2 up (i.e., maintains the cuff 2 in an unrolled position) to facilitate placement adjacent the target nerve TN and automatic wrapping of the cuff 2 around the target nerve TN, but the conformity of the cuff's 2 shape to the slider distal end 20 can also create a low profile. The low profile may reduce the risk of inadvertent contact with, and thus injury to, surrounding vessels, nerves, and tissue. The low profile can also enable a surgeon to minimize the size of the incision site, and further prevent inadvertent widening of the incision site and/or abrasion of the tissue around the incision site.

The cuff 2 can be inserted into and/or onto the retainer mechanism 6 by placing the cuff bottom surface 16 against the slider upper surface 22 and securing the cuff 2 within and/or onto the retainer mechanism 6. The slider implement 4 can be used to position the cuff upper surface 14 against the target nerve TN so that the cuff upper surface 14 faces towards the target nerve TN, thus the cuff upper surface 14 makes contact with the target nerve TN when the cuff 2 wraps around the target nerve TN.

In an exemplary embodiment, the slider implement 4 can include at least one tab 26 (e.g., holding tab) as the retainer mechanism 6. The tab(s) 26 can be formed onto a surface of the slider implement 4, which may be on the slider upper surface 22 of the slider distal end 20. For example, the tab(s) 26 can be protrusions that have been previously cut and formed out of the material of the slider implement 4. As shown in FIG. 2, a tab 26 can be an "L" shaped protrusion extending from the slider upper surface 22, wherein a channel 27 can be formed within a volume of space defined by an extending tab portion 28, a top tab portion 30, and the slider upper surface 22. The channel 27 can be used to slidably receive a portion of the cuff 2 and be retained therein. In some embodiments, the tab(s) 26 can be flexible, deflectable, rotatable, bendable, etc. For example, the tab(s) 26 can be bendable to facilitate rotating the top tab portion 30 relative to the extending tab portion 28. In some embodiments, a plurality of tabs 26 can be formed on the slider upper surface 22. As shown in FIGS. 1 and 3B, and as a non-limiting example, the plurality of tabs 26 can be arranged in a square or rectangular formation so that a square or rectangular cuff 2 can be retained by the retainer mechanism 6 by a plurality of tabs 26, preferably at least two tabs 26, located on one or more sides of the cuff 2.

The tab(s) 26 can hold the cuff 2 into a shape conformal with a portion of the slider implement 4. The slider implement 4 can then be used to insert the cuff 2 into the incision site and position the cuff 2 adjacent the target nerve TN, as described above. The tab(s) 26 can be manipulated to no longer retain the cuff 2 and/or allow the cuff 2 to advance toward its naturally rolled position. Manipulation of the tab(s) 26 can be achieved by bending the top tab portion 30 up and away from the cuff 2 held within the channel 27. As described earlier, the cuff 2 can then return to its naturally rolled state and envelop and/or encapsulate at least a portion of the target nerve TN. For example, when the cuff 2 has been moved to the proper position with the slider implement 4, the tab(s) 26 on the slider implement 4 can be caused to be bent up and away from the cuff 2, allowing the cuff 2 to roll up, encapsulating the target nerve TN. The slider implement 4 can then be removed from the incision site to complete the implantation procedure.

Figure 4A:
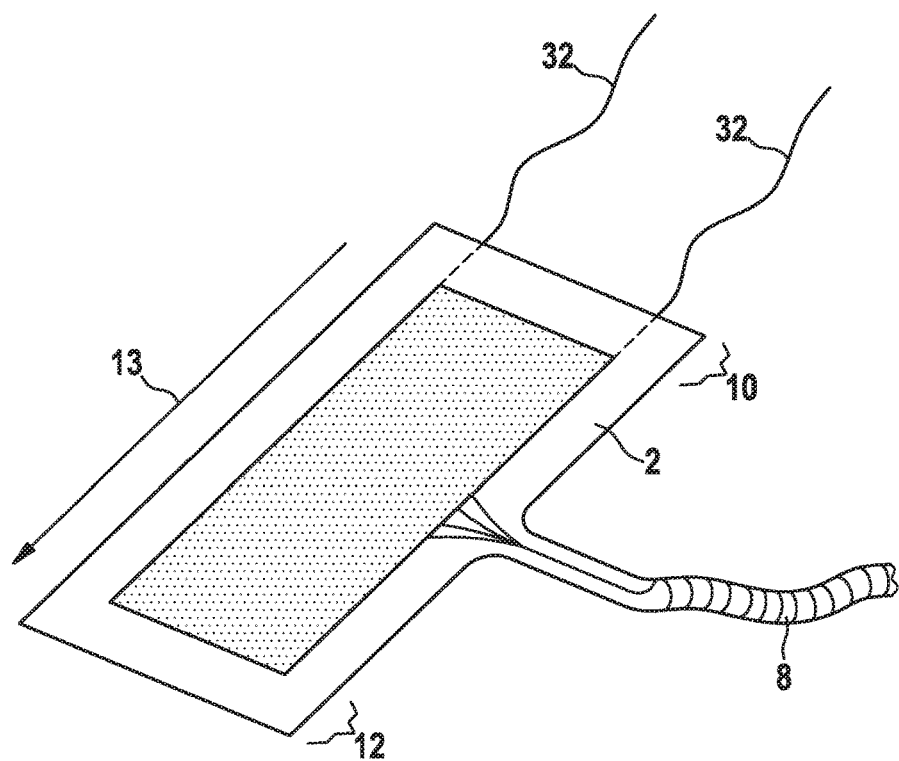
FIGS. 4A and 4B show an embodiment of an exemplary cuff with an assist-string in an unrolled position and in a rolled position, respectively, that may be used with the inventive system.
Figure 4B:
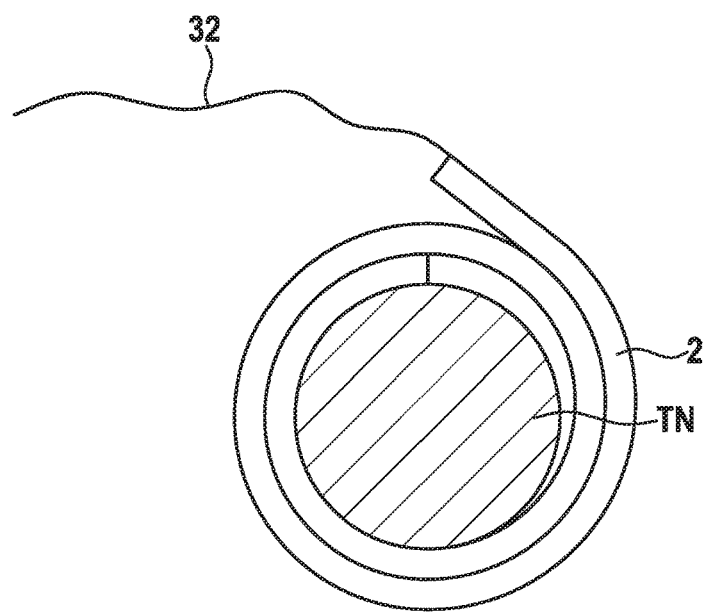

Referring to FIGS. 4A and 4B, additionally, the system 1 can include at least one assist-string 32. The assist-string 32 can be a suture thread, a nylon string or rope, a flexible metal cable, etc. used to control the rolling or unrolling of the cuff 2. The string(s) 32 can be attached to the cuff bottom surface 16 and/or formed within an interior of the cuff 2. The string(s) 32 can be made to run along at least a portion of the cuff 2 in a direction from the cuff proximal end 10 to the cuff distal end 12 and extend from the cuff proximal end 10 so that a distal end(s) of the string(s) 32 can be grasped with a hand, forceps, tweezers, etc. The string(s) 32 can then be tugged upon and/or selectively released to provide a means to control the transition of the cuff 2 from the unrolled to the rolled position. For example, once the retainer mechanism 6 is actuated and the cuff 2 is allowed to advance towards the rolled position, the string(s) 32 can be grasped to arrest and control the cuff's 2 transition from the unrolled to the rolled position. A user can then controllably release and/or pull on the string(s) 32 to cause the cuff 2 to transition to and from the unrolled and rolled positions, or any intermediary position.

As shown in FIG. 4A, in one form the cuff 2 has a thin to thick structure extending from its proximal end 10 to distal end 12, along arrow 13. When the cuff 2 is deployed, it is contemplated that the tabs 26 (see FIG. 3B) near the cuff 2 proximal end 10 will be bent or moved at least first, so that the proximal end 10 of the cuff 2 will first roll around the target nerve TN. But having the proximal end 10 of the cuff 2 thinner will facilitate ease of the cuff 2 returning to its naturally rolled state, as a thinner material will be more apt to curl. The thicker end can be at the distal end 12, as the cuff 2 will have already initiated its return to its naturally rolled state.

In an alternative embodiment, other arrangements of the plurality of tabs 26 can be used. Further, cuff 2 shapes other than a square or rectangle shape can be used. It is envisioned that various arrangement of the plurality of tabs 26 can be used to accommodate various shaped cuffs 2 and implantation procedures. For example, the tabs 26 on each side of the cuff 2 can be varied in number or by location. Further, the varying arrangements of the plurality of tabs 26 can be done to provide more stability for the cuff 2 (e.g., increased the number of tabs 26), provide for more ease during implantation (e.g., decrease the number of tabs 26), etc.

As shown in FIGS. 5-6, in an additional embodiment, the retainer mechanism 6 can include a debossed, or indented, section 34 formed within a portion of the slider implement 4. For example, the debossed section 34 can be formed into the slider upper surface 22 so as to form a depression within the slider implement 4. The debossed section 34 can be configured (length, width, depth, shape) to complement the configuration of the cuff 2 so that the cuff 2 can be placed within the debossed section 34 so that the cuff 2 profile is container within that of the slider implement 4. The debossed section 34 can be used as an alternative to or in addition to any other retainer mechanism 6 described herein. For example, the debossed section 34 can be formed within an area of the slider implement 4 that is adjacent any one of the tab(s) 26. In some embodiments, the debossed section 34 is formed within an area of the slider implement 4 that is surrounded or enveloped by the arrangement of the plurality of tabs 26. When the cuff 2 is secured within the debossed section 34, the cuff's 2 profile may be at least partially contained within that of the slider implement 4. This can facilitate a smoother surface of the slider implement 4, and thus further prevent abrasion during implantation. For example, the debossed section 34 can be configured to receive the cuff 2 within the depression so that the cuff upper surface 14 is flush with the slider upper surface 22. Further, any one or all of the tab(s) 26 can be formed within the debossed section 34. In some embodiments, the tab(s) 26 placed within the debossed section 34 can be configured to not extend beyond the slider upper surface 22, which may include an upper surface of the top tab portion(s) 30 being flush with the slider upper surface 22.

Still in reference to FIGS. 5-6, in one form, the retainer mechanism 6 can include a pull tab 36 that may run alongside and/or within the slider implement 4 (e.g., in slider slot 42) from the slider proximal end 18 to a debossed section 34 at or close to the slider distal end 20 of the slider implement 4. The pull tab 36 can be slidingly engaged with the slider implement 4. In this form, the retainer mechanism 6 includes at least one distal tab 39 located at or near a distal end of the debossed section 34 and at least one proximal tab 41 located at or near a proximal end of the debossed section 34. The distal tab 39 is connected to the slider implement 4. The proximal tab 41 is in mechanical connection with the pull tab, such that moving the pull tab 36 effectuates movement of the proximal tab 41. The pull tab 36 may be grasped with a hand, forceps, tweezers, etc. The pull tab 36 is slidingly engaged with the slider implement 4 so as to enable slidable motion of the pull tab 36, and thus manipulation of the proximal tab 41. For example, the pull tab 36 can be an elongated member that is slid into a track or channel formed within or onto the slider implement 4, enabling slidable motion of the pull tab 36 along the forward proximal-distal direction 38 and rearward distal-proximal direction 40. Pulling the pull tab 36 so as to cause it to move toward the slider proximal end 18 (i.e., movement toward the rearward distal-proximal direction 40) can cause the proximal tab 41 to be manipulated and move toward the proximal end 18 and release the cuff 2.

For example, the cuff 2 can be temporarily held within in the debossed section 34 of the slider implement 4 with the distal tab 39 and the proximal tab 41. The distal tab 39 may be affixed to the slider implement 4 at or near the distal end of the debossed section 34. The proximal tab 41 can be located at or near the proximal end of the debossed section 34, where the pull tab 36 is fed through the slider implement 4, the actuation thereof allowing the proximal tab 41 to be extended and retracted. Thus, the proximal tab 41 can also be slidingly engaged with the slider implement 4. Placing the proximal tab 41 in the extended position would cause the proximal tab 41 to extend over a portion of the cuff 2 that has been placed within the debossed section 34, and thus prevent the cuff 2 from transitioning into the rolled position. Placing the proximal tab 41 in the retracted position would cause the proximal tab 41 to not extend over any portion of the cuff 2 that has been placed within the debossed section 34, and thus allowing the cuff 2 to transition into the rolled position. An assist-string(s) 32 (see FIGS. 4A-4B) could be used to control the rolling or unrolling of the cuff 2, as described above.

Figure 5A:
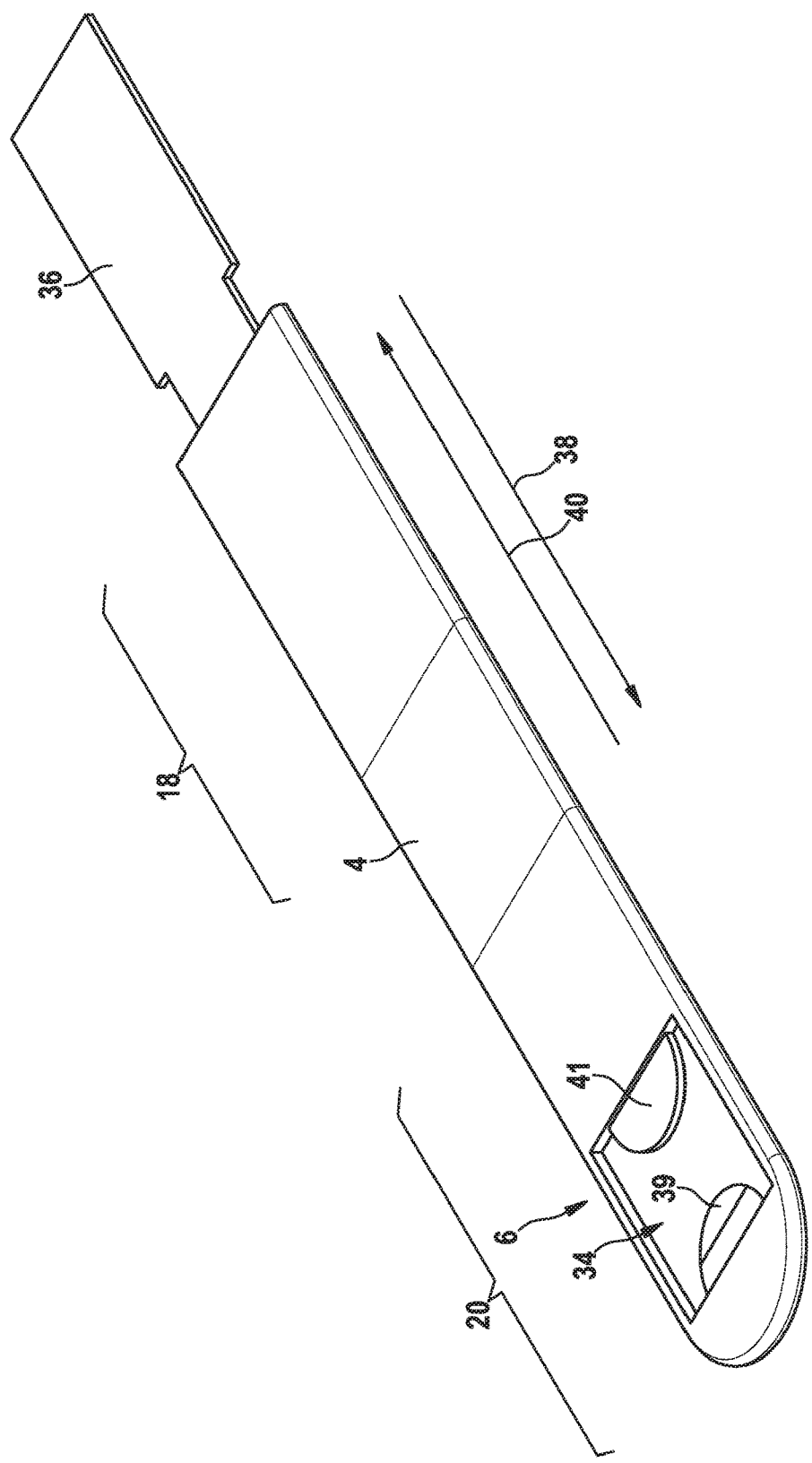
FIGS. 5A-5F show various views an embodiment of the system with a slider implement and a pull tab as part of the retainer mechanism.
Figure 5B:
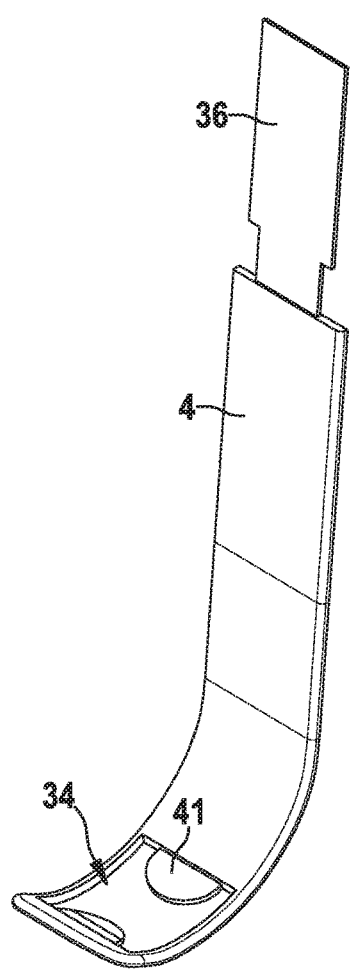
Figure 5C:
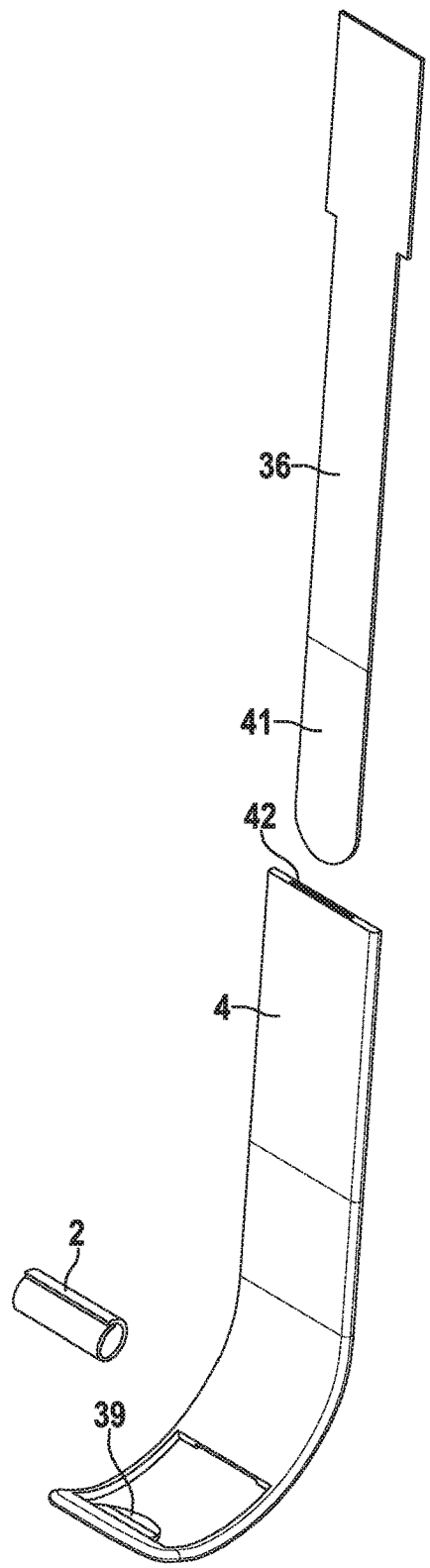
Figure 5D:
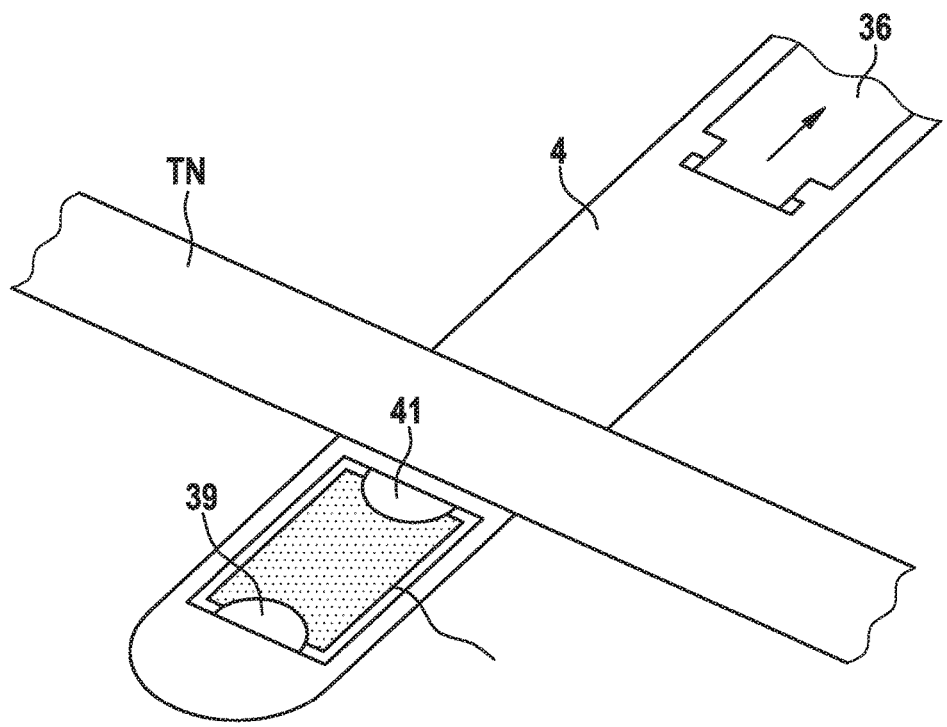
Figure 5E:
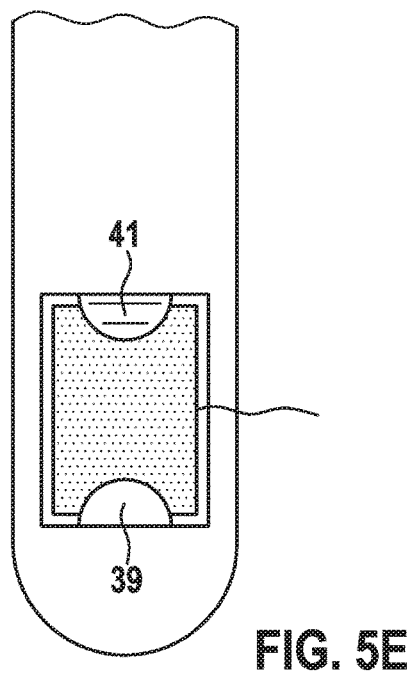
Figure 5F:
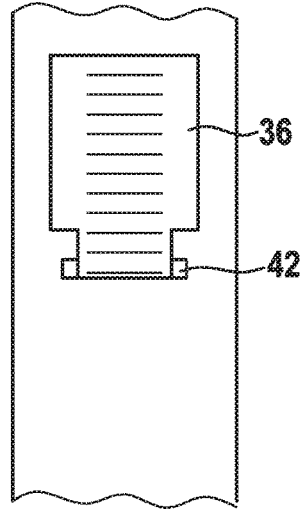

In a further embodiment, the distal end of the pull tab 36 can be the proximal tab 41, as shown in FIGS. 5A-5C. In this embodiment, the slider implement 4 can include a slider slot 42 extending from a slider proximal end 18 to the proximal end of the debossed section 34. The pull tab 36 can be inserted into the slider slot 42 with the distal end of the pull tab 36 (e.g., the proximal tab 41) spearheading the insertion until the distal end of the pull tab 36 enters the debossed section 34 thus forming the proximal tab 41. The pull tab 36 can then be actuated along the forward proximal-distal direction 38 and rearward distal-proximal direction 40 to secure and release the cuff 2 in a manner as previously described.

In operation, and as shown in FIGS. 6A to 6D, the cuff 2 is secured in the debossed portion 34 (FIG. 5A. The slider implement 4 is placed in the incision and moved so that the cuff 2 is under the target nerve TN (e.g., vagal nerve) (see FIG. 6A). The pull tab 36 is moved in the rearward distal-proximal direction, shown by arrow 40, to move the proximal tab 41 back into the slider implement 4 and release the cuff 2 proximal end 10 (see FIG. 6B) This allows the cuff 2 to transition to the rolled position around the target nerve TN. The slider implement 4 is then pushed or extended into the incision (arrow 38) to release the cuff 2 distal end 12 from the distal tab 39 (see FIG. 6C). This allows the cuff 2 to roll completely around the target nerve TN. The slider implement 4 is then removed from the incision in proximal direction (arrow 40), with the cuff 2 being secured around the target nerve TN (see FIG. 6D).

It is noted that with such embodiments, there is no need to bend any tab(s) 26 because manipulation of the proximal tab 41 is achieved by slidable motion of the pull tab 36. This can further reduce risk of damaging the target nerve TN, other nerves, vessels, and/or surrounding tissue. As seen in FIGS. 5A-5C, the distal tabs 39 and proximal tabs 41 are both within the debossed section 34 when retaining the cuff 2, and the proximal tab 41 is slid within the slider slot 42 when releasing the cuff 2, thus reducing the overall profile. Again, an assist-string(s) 32 (see FIGS. 4A-4B) could be used to control the rolling or unrolling of the cuff 2, as described above. It is further contemplated that this version of the retainer mechanism 6 can be used as an alternative to or in addition to any of the retainer mechanisms 6 described herein.

Referring to FIGS. 7A to C, in an alternative embodiment, an embodiment of the inventive system with a retention slide 47 as part of the retainer mechanism is shown. FIG. 7A shows the inventive system comprising a slider implement 4, a retention slide 47 (or plunger) slidably received in a slider slot 42, which is formed into the slider implement, and a cuff 2, FIG. 7B shows the pull tab or retention slide 47 in detail, and FIG. 7C shows the retention slider in a sectional view along dotted line 7c in FIG. 7B. The retainer mechanism 6 can include one fixed tab 43, three movable tabs including one on the retention slide 47 (movable tab 44) and two on the cuff 2 (tabs 45). The fixed tab 43 anchors the distal end 12 of the cuff; the movable tab 44 anchors the proximal end 10 of the cuff; and tabs 45 on the cuff 2 engage arms 46 on the retention slide 47 to secure the midpoint of the cuff 2. The cuff 2 can be held in a debossed section 34 of the slider implement 4 so that its profile is contained within the slider implement 4. As the retention slide 47 is withdrawn, the movable tab 44 moves into the slider implement 4 and the proximal end 10 of the cuff 2 (with electrodes 48) is freed first, allowing the cuff 2 to roll up to its natural state only to its midpoint, where it remains held by engagement of the arms 46 on the retention slide 47 and the hold tabs 45 on the cuff 2. Continued pulling of the retention slide 47 imparts a pulling force on the cuff 2 by protrusions, or teeth, 52 formed on the arms 46 of the retention slide 47 (FIG. 7C) engaging the hold tabs 45 on the cuff 2. This causes the distal end 12 of the cuff 2 to be pulled free from the tab 43, followed by a release of the arms 46 against the tabs 45 (or a release against the cuff 2 directly), which frees the cuff 2 from the slider implement 4 enabling the cuff 2 to wrap around the target nerve TN.

Referring to FIG. 8, in an alternative embodiment, the retainer mechanism can include a cuff-retention slot 54 with a plunger 56. The cuff-retention slot 54 is an aperture formed into the distal end 20 of the slider implement 4 that slidably receive and temporarily retains the cuff 2 in an unrolled position. The cuff 2 is loaded into the slot 54 in the slider 4 and pulled open from its naturally closed state. In this embodiment, however, the end of the cuff 2 with the electrodes 48 would be received last, as it will be the first end deployed to wrap around the target nerve TN. The cuff 2 and the plunger 56 include cooperating mating features, shown at 58, 59, which allow the cuff 2 to be pulled into and pushed out of the slider 4. One example of a mating feature are holes or indentations 58 (e.g. two small holes) in or at the proximal end of the cuff 2, along with matching protrusions 59 in or at the distal end or the plunger 56. When the cuff and plunger are both confined by the slider 4, the protrusions 58' engage with the holes or indentations 58 in the cuff 2. The result is that cuff 2 is locked to the plunger 56 and moves with the plunger. When the cuff 2 is deployed, the plunger pushes it out of the slider 4. When the proximal portion of the plunger 56 is pushed completely into the slider 4, the distal portion of the plunger passes out of slot 54 of slider 4. At this point the cuff 2 is no longer confined by slider 4, and the protrusions 59 will disengage with the cuff indentations 58. The cuff is released and wrapped around the target nerve TN. Slider 4 and plunger 56 can be removed.

In this embodiment, the plunger 56 is elongated member structured to be slidably inserted into the slider slot 42 with the distal end of the plunger 56 spearheading the insertion until the distal end of the plunger 56 mates with the cuff 2. The plunger 56 is pulled back to pull the cuff 2 into the retention slot, thus unrolling the cuff 2 therein. The slider is slid under the target nerve and the plunger 56 is pushed forward forces the cuff 2 out of the slot 54 and the slider 4. During such deployment, the cuff 2 exits the open slot 54 and the cuff 2 can naturally curl into its spiral shape around the target nerve.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

REFERENCE LIST

1 System (for implanting a nerve cuff)
2 (Nerve) Cuff
4 Slider implement
6 Retainer mechanism
8 Electrode lead
10 Cuff proximal end
12 Cuff distal end
13 Arrow, showing thin to thick structure of the cuff
14 Cuff upper surface
16 Cuff bottom surface
18 Slider proximal end
20 Slider distal end
22 Slider upper surface
24 Slider bottom surface
26 Tab (included in slider implement)
27 Channel (formed by tab)
28 Extended tab portion
30 Top tab portion
32 Assist strings
34 (debossed) Section
36 Pull tab
38 Forward proximal distal direction
39 Distal tab
40 Rearward distal proximal direction
41 Proximal tab
42 Slider slot
43 Fixed tab
44 Movable tab
45 Tabs (on cuff)
46 Arms
47 Pull tab or retention slide
48 Electrodes (on cuff)
52 Protrusions or teeth on arms
54 Cuff-retention slot
56 Plunger
58 Indentations in the cuff
59 Matching protrusions 59
TN Target Nerve (e.g. vagal nerve)

We claim:

1. A system for implanting a nerve cuff, comprising:
a nerve cuff comprising a flat, flexible material having distal and proximal ends, wherein the nerve cuff is biased to a naturally coiled shape; and
a slider implement configured to deploy the nerve cuff and wrap the nerve cuff around a target nerve, the slider implement comprising:
an elongated member having a slider proximal end and a slider distal end;
a retainer mechanism provided on the slider distal end, the retainer mechanism configured to temporarily retain the nerve cuff in an uncoiled state within and/or on the slider implement,
wherein the slider distal end is configured to insert into an incision and position the nerve cuff adjacent the target nerve,
wherein actuation of the retainer mechanism releases the nerve cuff from the slider implement such that the nerve cuff transitions from the uncoiled state to the coiled state allowing the nerve cuff to wrap around the target nerve, and
wherein the retainer mechanism comprises a debossed section formed within a portion of the slider implement at the slider distal end configured for receiving the nerve cuff in the uncoiled state.

2. The system of claim 1, wherein the nerve cuff comprises an electrode nerve cuff.

3. The system of claim 1, wherein:
the retainer mechanism comprises at least one tab formed on a surface of the slider distal end; and
actuation of the retainer mechanism comprises manipulation of the at least one tab.

4. The system of claim 1, wherein the retainer mechanism comprises:
a fixed tab disposed on the slider distal end and extending over the debossed section; and
a movable tab provided on a distal end of a pull tab received in a slot formed in the slider implement, the movable tab extending into the debossed section to maintain the nerve cuff in the debossed section, and wherein the pull tab is movable to retract the movable tab into the slider slot to release the nerve cuff for deployment about the target nerve.

5. The system of claim 1, wherein the retainer mechanism comprises:
a fixed tab disposed on the slider distal end and extending over the debossed section;
a movable tab provided on a distal end of a pull tab received in a slot formed in the slider implement, the movable tab extending into the debossed section to maintain the nerve cuff in the debossed section; and
arms extending from the pull tab distal end past the movable tab, the arms extending into the debossed section to maintain the nerve cuff in the debossed section,
wherein the pull tab is movable to retract the movable tab into the slider slot to release an end the nerve cuff for deployment about the target nerve, wherein the arms engage the nerve cuff permitting the nerve cuff to coil only up to a midpoint,
wherein further movement of the pull tab causes teeth formed on the arms to engage tabs on the nerve cuff to disengage the nerve cuff from the fixed tab enabling the nerve cuff to fully wrap around the target nerve.

6. The system of claim 1, wherein:
the retainer mechanism comprises a cuff-retention slot formed into the slider distal end, the cuff retention slot comprising an aperture used to slidably receive and temporarily retain the electrode cuff in the unrolled position within the slider implement;
a slider slot is formed into the slider implement extending from the slider proximal end to the slider distal end and leading into the cuff-retention slot;
the system further comprises a plunger slidably received in the slider slot;
movement of the plunger in a forward proximal-distal direction causes the nerve cuff retained within the cuff-retention slot to exit the cuff-retention slot by exiting the slider distal end, and as the electrode cuff exits the slider distal end it begins to transition to the coiled position.

7. The system of claim 6, wherein the nerve cuff and plunger include cooperating mating elements which are configured to enable the plunger to pull the nerve cuff into the cuff-retention slot and push the nerve cuff out of the cuff retention slot for deployment about the target nerve.

8. The system recited in claim 1, further comprising at least one assist-string attached to the nerve cuff, wherein the at least one assist-string enables controlled coiling of the nerve cuff when deployed about the target nerve.

9. A tool for implanting a nerve cuff, comprising:
a slider implement configured to deploy the nerve cuff and wrap the nerve cuff around a target nerve, the slider implement comprising:
an elongated member having a slider proximal end and a slider distal end;
a retainer mechanism provided on the slider distal end, the retainer mechanism configured to temporarily retain the nerve cuff in an uncoiled state within and/or on the slider implement,
wherein the slider distal end is configured to insert into an incision and position the nerve cuff adjacent the target nerve,
wherein actuation of the retainer mechanism releases the nerve cuff from the slider implement such that the nerve cuff transitions from the uncoiled state to the coiled state allowing the nerve cuff to wrap around the target nerve, and
wherein the retainer mechanism comprises a debossed section formed within a portion of the slider implement at the slider distal end configured for receiving the nerve cuff in the uncoiled state.

10. The tool of claim 9, wherein the nerve cuff comprises an electrode nerve cuff.

11. The tool of claim 9, wherein:
the retainer mechanism comprises at least one tab formed on a surface of the slider distal end; and
actuation of the retainer mechanism comprises manipulation of the at least one tab.

12. The tool of claim 9, wherein the retainer mechanism comprises;
a fixed tab disposed on the slider distal end and extending over the debossed section; and
a movable tab provided on a distal end of a pull tab received in a slot formed in the slider implement, the movable tab extending into the debossed section to maintain the nerve cuff in the debossed section, and wherein the pull tab is movable to retract the movable tab into the slider slot to release the nerve cuff for deployment about the target nerve.

13. The system of claim 9, wherein the retainer mechanism comprises:
a fixed tab disposed on the slider distal end and extending over the debossed section;
a movable tab provided on a distal end of a pull tab received in a slot formed in the slider implement, the movable tab extending into the debossed section to maintain the nerve cuff in the debossed section; and
arms extending from the pull tab distal end past the movable tab, the arms extending into the debossed section to maintain the nerve cuff in the debossed section,
wherein the pull tab is movable to retract the movable tab into the slider slot to release an end the nerve cuff for deployment about the target nerve, wherein the arms engage the nerve cuff permitting the nerve cuff to coil only up to a midpoint,
wherein further movement of the pull tab causes teeth formed on the arms to engage tabs on the nerve cuff to disengage the nerve cuff from the fixed tab enabling the nerve cuff to fully wrap around the target nerve.

14. The tool of claim 9, wherein:
the retainer mechanism comprises a cuff-retention slot formed into the slider distal end, the cuff retention slot comprising an aperture used to slidably receive and temporarily retain the electrode cuff in the unrolled position within the slider implement;
a slider slot is formed into the slider implement extending from the slider proximal end to the slider distal end and leading into the cuff-retention slot;
the tool further comprises a plunger slidably received in the slider slot;
movement of the plunger in a forward proximal-distal direction causes the nerve cuff retained within the cuff-retention slot to exit the cuff-retention slot by exiting the slider distal end, and as the electrode cuff exits the slider distal end it begins to transition to the coiled position.

15. The tool of claim 14, wherein the nerve cuff and plunger include cooperating mating elements which are configured to enable the plunger to pull the nerve cuff into the cuff-retention slot and push the nerve cuff out of the cuff-retention slot for deployment about the target nerve (TN).

16. The tool recited in claim 9, further comprising at least one assist-string attached to the nerve cuff, wherein the at least one assist-string enables controlled coiling of the nerve cuff when deployed about the target nerve.

17. The tool of claim 9, the retainer mechanism holds the nerve cuff into a shape conformal with the slider distal end.

18. A method for implanting a nerve cuff, the method comprising:
temporarily securing a nerve electrode cuff in an uncoiled position within a debossed section formed in a slider implement at a slider distal end via a retainer mechanism, wherein the retainer mechanism comprises a fixed tab connected to the slider implement, and a movable tab provided on a distal end of a pull tab received in a slot formed in the slider implement, the fixed tab and movable tab extending into the debossed section and engaging the nerve cuff to temporarily maintain the nerve cuff in the debossed section,
creating an incision into a body of a being and excising a target nerve to create an incision site either before or after the electrode cuff is temporarily secured to the retainer mechanism;

inserting at least a portion of the slider implement and the nerve cuff through the incision and advancing the nerve cuff into the incision site so that the nerve cuff is placed adjacent to the excised target nerve;

moving the movable tab back into the slot to release a proximal end of the nerve cuff;

pushing the slider implement further into the incision thus releasing the distal end of the nerve cuff from the fixed tab thereby permitting the nerve cuff to wrap around the target nerve; and, removing the slider implement from the incision site.

19. A method for implanting a nerve cuff, the method comprising:

causing the nerve cuff to unroll from its naturally rolled position;

temporarily securing the nerve cuff in an unrolled position within and/or on a slider implement via a retainer mechanism, wherein the retainer mechanism comprises a debossed section formed within a portion of the slider implement at the slider distal end configured for receiving the nerve cuff in the unrolled position;

creating an incision into a body of a being and excising a target nerve to create an incision site either before or after the electrode cuff is secured to the retainer mechanism;

inserting at least a portion of the slider implement and the electrode cuff through the incision and advancing the nerve cuff into the incision site so that the nerve cuff is placed adjacent to the excised target nerve;

actuating the retainer mechanism, allowing the nerve cuff to advance toward its naturally rolled position, wherein transitioning from the unrolled position to the rolled position is uninterrupted or performed in a staged fashion;

allowing the nerve cuff to wrap around the target nerve; and removing the slider implement from the incision site.

* * * * *